United States Patent
Itu et al.

(10) Patent No.: US 11,030,490 B2
(45) Date of Patent: Jun. 8, 2021

(54) PERFORMANCE OF MACHINE LEARNING MODELS FOR AUTOMATIC QUANTIFICATION OF CORONARY ARTERY DISEASE

(71) Applicant: Siemens Healthcare GmbH, Erlangen (DE)

(72) Inventors: Lucian Mihai Itu, Brasov (RO); Tiziano Passerini, Plainsboro, NJ (US); Thomas Redel, Poxdorf (DE); Puneet Sharma, Princeton Junction, NJ (US)

(73) Assignee: Siemens Healthcare GmbH, Erlangen (DE)

( * ) Notice: Subject to any disclaimer, the term of this patent is extended or adjusted under 35 U.S.C. 154(b) by 161 days.

(21) Appl. No.: 16/556,324

(22) Filed: Aug. 30, 2019

(65) Prior Publication Data

US 2021/0064936 A1 Mar. 4, 2021

(51) Int. Cl.
| | | |
|---|---|---|
| *G06K 9/62* | (2006.01) | |
| *G06T 7/00* | (2017.01) | |
| *A61B 5/00* | (2006.01) | |
| *A61B 5/02* | (2006.01) | |
| *A61B 5/026* | (2006.01) | |
| *A61B 5/318* | (2021.01) | |

(52) U.S. Cl.
CPC .......... *G06K 9/6263* (2013.01); *A61B 5/026* (2013.01); *A61B 5/02007* (2013.01); *A61B 5/318* (2021.01); *A61B 5/7267* (2013.01); *G06K 9/6254* (2013.01); *G06T 7/0012* (2013.01); *G06T 2207/20081* (2013.01); *G06T 2207/20101* (2013.01); *G06T 2207/30104* (2013.01)

(58) Field of Classification Search
CPC ..... A61B 5/02007; A61B 5/026; A61B 5/318; A61B 5/7267; G06K 9/6254; G06K 9/6263; G06T 2207/20081; G06T 2207/20101; G06T 2207/30104; G06T 7/0012

See application file for complete search history.

(56) References Cited

U.S. PATENT DOCUMENTS

| | | |
|---|---|---|
| 9,349,178 B1 | 5/2016 | Itu et al. |
| 10,290,101 B1 * | 5/2019 | Podilchuk ............... G06T 11/00 |
| 2013/0129165 A1 | 5/2013 | Dekel et al. |
| 2013/0129265 A1 | 5/2013 | Jaehrling et al. |

(Continued)

OTHER PUBLICATIONS

Choy et al., "3D-R2N2: A Unified Approach for Single and Multi-view 3D Object Reconstruction", European conference on Computer Vision—ECCV Apr. 2016, Springer Cham, Part of the Lecture Notes in Computer Science, vol. 9912, 18 pgs.

(Continued)

*Primary Examiner* — Manuchehr Rahmjoo (57) ABSTRACT

Systems and methods for retraining a trained machine learning model are provided. One or more input medical images are received. Measures of interest for a primary task and a secondary task are predicted from the one or more input medical images using a trained machine learning model. The predicted measures of interest for the primary task and the secondary task are output. User feedback on the predicted measure of interest for the secondary task is received. The trained machine learning model is retrained for predicting the measures of interest for the primary task and the secondary task based on the user feedback on the output for the secondary task.

20 Claims, 6 Drawing Sheets

(56) References Cited

U.S. PATENT DOCUMENTS

2014/0219548 A1 8/2014 Wels et al.
2019/0130578 A1* 5/2019 Gulsun ............... G06N 3/0445

OTHER PUBLICATIONS

Amershi, "Power to the People: the Role of Humans in Interactive Machine Learning", AI Magazine, Association for the Advancement of Artificial Intelligence, 2014, vol. 35, No. 4, pp. 105-120.
Lin et al., "Interactive Multi-Task Relationship Learning", IEEE 16th International Conference on Data Management, 2016, 10 pgs.
Zhang et al., "An Overview of Multi-Task Learning", National Science Review, 2018, vol. 5, pp. 30-43.
European Patent Application No. 18464002.7 filed Sep. 13, 2018, pp. 1-32.
Passerini et al., "System and Method for Medical Image Augmentation Based on Deep Learning and Computational Modeling", Siemens, 2018, 7 pgs.
Partial European Search Report dated Feb. 27, 2020 in corresponding European Patent Application No. 19464014.0.

* cited by examiner

PERFORMANCE OF MACHINE LEARNING MODELS FOR AUTOMATIC QUANTIFICATION OF CORONARY ARTERY DISEASE

TECHNICAL FIELD

The present invention relates generally to improving performance of machine learning models, and more particularly to improving performance of machine learning models for automatic quantification of coronary artery disease based on user feedback.

BACKGROUND

Machine learning models have been applied to perform various tasks for an increasing number of applications. In one example, machine learning models have been applied to characterize coronary artery disease by predicting a functional severity of coronary lesions. Such machine learning models may be trained using labeled training images to map a set of input features to a predicted output value to perform a task. In supervised learning, during the training phase, the machine learning model is refined to maximize prediction accuracy by evaluating an output predicted from the training images against its label. Machine learning models are typically trained for a specific task.

A number of challenges are associated with such machine learning models. One challenge is generalization—that trained machine learning models may not be able to be properly generalized for unseen data. Such is the case where the trained machine learning model is too specific for the training images or for the task for which it is trained. Another challenge is control—that there may be no direct way for a user to validate the proper behavior of the trained machine learning model, such as where the trained machine learning model predicts an fractional flow reserve (FFR) value. An additional challenge is feedback—that a user may not be able to easily provide feedback to improve performance of the trained machine learning model since input features may not be easily recognizable or easily evaluated by the user.

BRIEF SUMMARY OF THE INVENTION

In accordance with one or more embodiments, systems and methods for online retraining of a trained machine learning model are provided. One or more input medical images are received. Measures of interest for a primary task and a secondary task are predicted from the one or more input medical images using a trained machine learning model. The predicted measures of interest for the primary task and the secondary task are output. User feedback on the predicted measure of interest for the secondary task is received. The trained machine learning model is retrained for predicting the measures of interest for the primary task and the secondary task based on the user feedback on the output for the secondary task.

In one embodiment, the measure of interest for the primary task cannot be directly validated by a user from the one or more input medical images and the measures of interest for the secondary task can be directly validated by the user from the one or more input medical images. The measure of interest for the primary task may include a hemodynamic index, such as, e.g., a virtual fractional flow reserve. The measures of interest for the secondary task may include at least one of a location of a measurement point, a location of a common image point, a location of a stenosis, and a segmentation of a vessel.

In one embodiment, the user feedback may include an acceptance or a rejection of the predicted measure of interest for the secondary task, or a modification to the predicted measure of interest for the secondary task.

In one embodiment, a measure of confidence may also be determined. The measure of confidence may be determined by predicting additional measures of interest for the primary task and the secondary task from the one or more input medical images using the retrained machine learning model, and determining a measure of confidence in the additional predicted measures of interest for the primary task and the secondary task based on a difference between the measures of interest predicted using the trained machine learning model and the additional measures of interest predicted using the retrained machine learning model. The measure of confidence may also be determined by predicting the measures of interest for the primary task and the secondary task from a single input medical image from a first sequence of images and a single input medical image from the second sequence of images using the trained machine learning model, predicting additional measures of interest for the primary task and the secondary task from two input medical images from the first sequence of images and two input medical image from the second sequence of images using the trained machine learning model, and determining a measure of confidence in the predicted measures of interest and/or the additional predicted measures of interest for the primary task and the secondary task based on a difference between 1) the measures of interest predicted from the single input medical image from the first sequence of images and the single input medical image from the second sequence of images using the trained machine learning model, and 2) the additional measures of interest predicted from the two input medical image from the first sequence of images and the two input medical image from the second sequence of images using the trained machine learning model.

In one embodiment, the one or more input medical images are selected by receiving respective electrocardiogram signals acquired during acquisition of a first sequence of images and a second sequence of images, associating an index with each image in the first sequence of images and the second sequence of images based on their respective electrocardiogram signals, matching images of the first sequence of images with images of the second sequence of images based on their associated index, and selecting an image of the first sequence and an image of the second sequence that match as the one or more input medical images.

These and other advantages of the invention will be apparent to those of ordinary skill in the art by reference to the following detailed description and the accompanying drawings.

DETAILED DESCRIPTION

The present invention generally relates to methods and systems for improving performance of machine learning models based on user feedback. Embodiments of the present invention are described herein to give a visual understanding of methods for improving performance of machine learning models based on user feedback. A digital image is often composed of digital representations of one or more objects (or shapes). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system.

Further, it should be understood that while the embodiments discussed herein may be discussed with respect to improving performance of a machine learning model trained to predict a measure of interest from one or more input medical images, the present invention is not so limited. Embodiments of the present invention may be applied for improving the performance of machine learning models trained to predict any measure of interest for performing any type of task using any type of input.

In accordance with one or more embodiments, systems and methods are provided for improving performance of a trained machine learning model based on user feedback. The trained machine learning model is trained to predict measures of interest for a plurality of tasks: a primary task and one or more secondary tasks. The measure of interest for the primary task cannot be directly verified by a user, while the measures of interest for the one or more secondary tasks can be directly verified by the user. By training the trained machine learning model to predict measures of interest for the one or more secondary tasks in addition to the primary task, the user may evaluate the one or more secondary tasks and provide such evaluation as user feedback for online retraining of the trained machine learning model. Advantageously, retraining the machine learning model with the user feedback on the measures of interest of the one or more secondary tasks improves performance (e.g., accuracy) of the trained machine learning model for predicting the measure of interest for all tasks (i.e., the primary task and the one or more secondary tasks).

Figure 1:
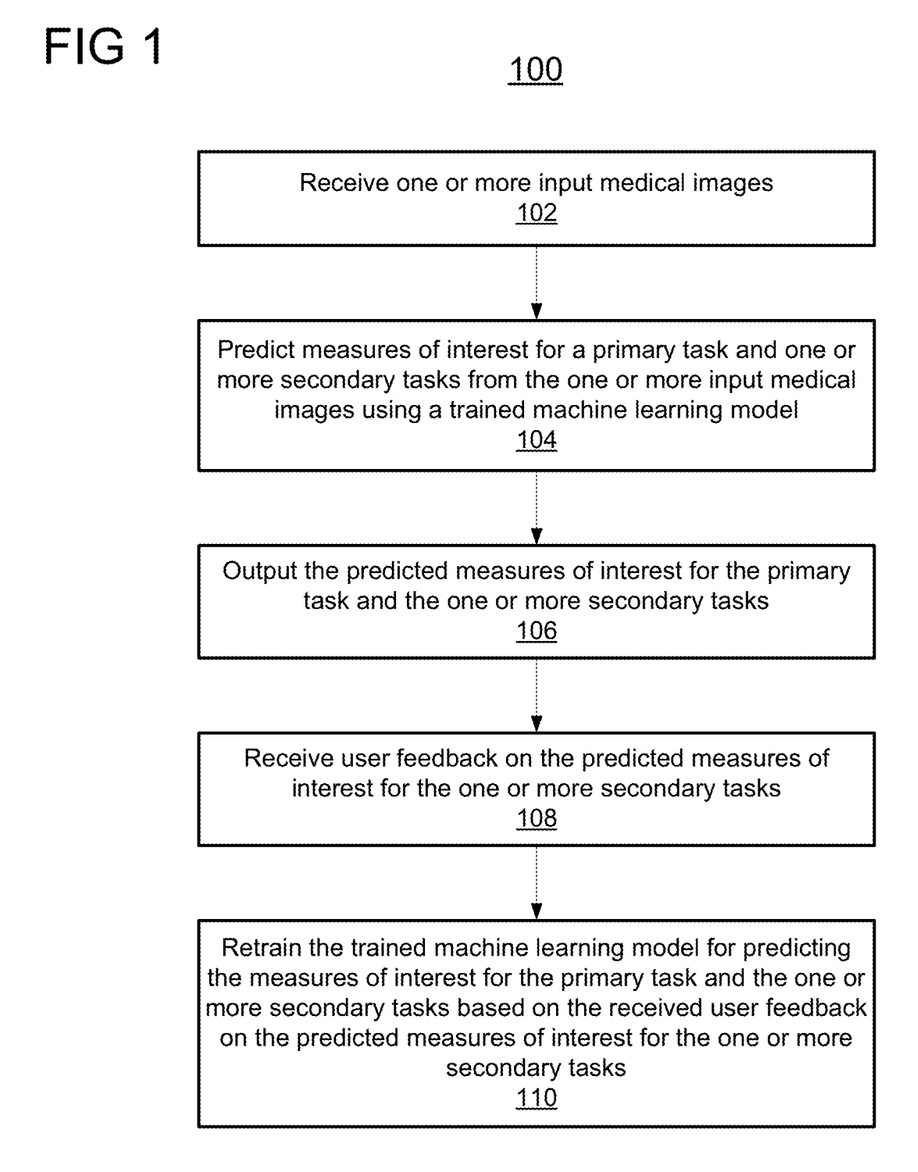
FIG. 1 shows a method for online retraining of a trained machine learning model based on user feedback.

FIG. 1 shows a method 100 for online retraining of a trained machine learning model for based on user feedback, in accordance with one or more embodiments. Method 100 is performed during an online or testing stage using a trained machine learning model. The trained machine learning model is trained during a prior offline or training stage, e.g., according to method 200 of FIG. 2, to perform a plurality of tasks: a primary task and one or more secondary tasks. The steps of method 100 may be performed by any suitable computing device, such as computer 602 of FIG. 6.

At step 102, one or more input medical images are received. The one or more input medical images may be any suitable images for performing the primary task and the one or more secondary tasks. The one or more input medical images may be of any suitable modality or combination of modalities, such as, e.g., computed tomography (CT), dynaCT, x-ray, magnetic resonance imaging (MRI), ultrasound (US), etc. The one or more input medical images may be received directly from an image acquisition device used to acquire the input medical image (e.g., image acquisition device 614 of FIG. 6), by loading previously acquired medical images from a storage or memory of a computer system, or by receiving medical images that have been transmitted from a remote computer system.

In one embodiment, the one or more input medical images include a pair (or more) of input medical images, each from a respective sequence of images. A sequence of images refers to a plurality of images of an object of interest acquired over a period of time. For example, the sequences of images may be angiographic sequences of coronary arteries. In one embodiment, the pair of input medical images are selected from their respective sequence of images by synchronizing the images in each respective sequence and selecting a synchronized or matching image from each sequence as the pair of input medical images, e.g., as described below with respect to FIG. 4.

In one embodiment, additional data may also be received with the one or more input medical images. The additional data may include any suitable data used for performing the primary task and the one or more secondary tasks. For example, the additional data may include patient data, such as, e.g., a priori acquired medical (imaging or non-imaging) data, past medical exams, etc. In another example, the additional data may include angulation information associated with the image acquisition device during acquisition of the one or more input medical images (e.g., angulation of the C-arm of the image acquisition device used to acquire each temporal sequence).

At step 104, measures of interest for a primary task and one or more secondary tasks are predicted from the one or more input medical images (and optionally the patient data, if any) using a trained machine learning model. The trained machine learning model may be trained during a prior training stage, e.g., according to method 200 of FIG. 2. The trained machine learning model may be based on any suitable machine learning model, such as, e.g., a neural network. In one embodiment, the trained machine learning model is a deep neural network. For example, the trained machine learning model may be based on a modified 3D Recurrent Reconstruction Neural Network (3D-R2N2). In one embodiment, the trained machine learning model is trained to predict the measures of interest for the primary task and the one or more secondary tasks using multi-task learning and to receive user feedback on the one or more secondary tasks for online retraining using interactive machine learning. The network structure of the trained machine learning model is discussed in further detail below with respect to FIG. 5, in accordance with one embodiment.

The primary task and the one or more secondary tasks may be any suitable tasks that are related or correlated. In one embodiment, the primary task and the one or more secondary tasks are related in that they may be performed based on the one or more input medical images. While embodiments described herein may refer to a primary task and one or more secondary tasks, it should be understood that any number of primary tasks and secondary tasks may be utilized.

The measure of interest for the primary task cannot be directly verified by a human user from the one or more input medical images. In one embodiment, the primary task includes predicting a functional measure or quantification of coronary artery disease at measurement locations (e.g., after each stenotic segment). For example, the measure of interest may be a value of a virtual fractional flow reserve (FFR), which is a functional measure for quantifying the hemodynamic significance of a stenosis in an artery. The FFR is typically determined based on the pressure drop over a coronary stenosis at hyperemia using invasive pressure wire based measurements. The virtual FFR seeks to replicate the FFR value via less invasive means. It should be understood that the measure of interest may be any other hemodynamic index, such as, e.g., a coronary flow reserve (CFR), an instantaneous wave free ratio (iFR), a basal stenosis resistance (BSR), a hyperaemic stenosis resistance (HSR), an index of microcirculatory resistance (IMR), or any other measure or quantification of coronary artery disease. In another embodiment, the primary task is a clinical decision (e.g., taken during or after an intervention), such as, e.g., whether or not to perform percutaneous coronary intervention (PCI) or coronary artery bypass grafting (CABG), an optimal medical therapy, a date of a next examination, etc.

The measures of interest for the one or more secondary tasks can be directly verified by the human user from the one or more input medical images. Examples of the one or more secondary tasks include predicting standard measurement locations in the input medical images, predicting a location of one or more common image points (e.g., common anatomical landmarks) in the input medical images, predicting a location of stenosis markers in the input medical images, predicting a location and anatomical significance of one or more stenoses in the input medical images, predicting a segmentation of one, several, or all vessels visible in the input medical images, predicting the thrombolysis in myocardial infarction (TIMI) frame count as a surrogate for the contrast agent velocity in the input medical images, predicting a healthy radius at all locations (e.g., in the case of diffuse disease and bifurcation stenosis) in the input medical images, predicting centerlines or a tree structure of vessels in the input medical images, predicting depth information of vessels (as a surrogate detecting vessel overlaps) in the input medical images, predicting myocardial territory associated with each main or side branch in the input medical images, etc. The one or more secondary tasks are determined during the training stage to maximize performance of the primary task, as further described below with respect to method 200 of FIG. 2.

At step 106, the predicted measures of interest for the primary task and the one or more secondary tasks are output. In one embodiment, outputting the predicted measures of interest for the primary task and the one or more secondary tasks includes visually displaying the predicted measures of interest, e.g., on a display device of a computer system. For example, the predicted measures of interest for the primary task and the one or more secondary tasks may be displayed along with the one or more medical images to facilitate user evaluation of the predicted measures of interest (e.g., for the one or more secondary tasks). Outputting the predicted measures of interest for the primary task and the one or more secondary tasks may also include storing the predicted measures of interest for the primary task and the one or more secondary tasks on a memory or storage of a computer system or transmitting the predicted measures of interest for the primary task and the one or more secondary tasks to a remote computer system.

At step 108, user feedback on the predicted measures of interest for the one or more secondary tasks is received. The one or more secondary tasks being directly verifiable by the user enable the user to provide such user feedback. The user feedback may be in any suitable form. In one embodiment, the user feedback is an acceptance or rejection by the user of the predicted measures of interest for the one or more secondary tasks. In another embodiment, the user feedback is user input correcting or modifying the predicted measures of interest for the one or more secondary tasks. For example, the user may interact with a user interface to select a common image point that is incorrectly predicted and move the common image point to a correct or desired location (e.g., in 2D or 3D space).

At step 110, the trained machine learning model is retrained for predicting the measures of interest for the primary task and the one or more secondary tasks based on the received user feedback on the predicted measures of interest for the one or more secondary tasks. In one embodiment, additional training data is formed comprising the one or more input medical images and the user feedback (as the ground truth value), and such additional training data is used to retrain the trained machine learning model, e.g., according to method 200 of FIG. 2. For example, if the user corrects a location of a common image point in one of the input medical images, the trained machine learning model is retrained using the one or more input medical images with the corrected location of the common image point as the ground truth value. In another example, if the user rejects the predicted measures of interest of the one or more secondary tasks, the rejected predicted measures of interest may be used as a negative example to retrain the trained machine learning model. Because of the shared layers of the machine learning model, such retraining based on user feedback on the predicted measures of interest for the one or more secondary tasks implicitly leads to updating the machine learning model for predicting the measures of interest for all tasks (i.e., the primary task and the one or more secondary tasks). The steps of method 100 may be performed any number of times for newly received one or more input medical images.

In one embodiment, the trained machine learning model may determine a measure of confidence in the predicted measures of interest based on how much the predicted measures of interest change after retraining. In particular, after predicting measures of interest for the primary task and the one or more secondary tasks using the trained machine learning model, additional measures of interest for the primary task and the one or more secondary tasks may be predicted using the retrained machine learning model. A measure of confidence in the measures of interest (predicted using the trained machine learning model) and/or in the additional measures of interest (predicted using the retrained machine learning model) may be determined based on a change or difference between the measures of interest and the additional measures of interest. In one example, after retraining the machine learning model for the secondary task of predicting a location of a common image point, the primary task of predicting an FFR value may change. Depending on a change or difference between the FFR values, a confidence level in the results can be determined. In one embodiment, the confidence level is based on a threshold, such that if the FFR value changes by more than a threshold amount (e.g., 0.1) after retraining, the confidence in the results is low.

In another embodiment, the trained machine learning model may provide a measure of confidence in the predicted measures of interest by applying the trained machine learning model a plurality of times for the one or more input medical images. In one example, the trained machine learning model may be applied a plurality of times, each time considering a different number of images from each temporal sequence. For instance, first predicted measures of interest may be obtained by considering as the one or more input medical images only a single 2D image from each temporal sequence, second predicted measures of interest may be obtained by considering as the one or more input medical images only two 2D images from each temporal sequence, etc. In another example, where the one or more input medical images comprise an image sequence over multiple heart beats and the behavior is assumed to be the same at each heartbeat, the trained machine learning model may be applied a plurality of times, each time on a different heartbeat. Depending on a change or difference between the predicted measures of interest each time the trained machine learning model is applied, a confidence measure may be determined (e.g., based on a threshold) for the first and/or second predicted measures of interest.

In another embodiment, the measure of confidence may be based on patient characteristics (e.g., age or other demographics, patient history) as well as image characteristics (e.g., how sharp is the transition from vessel to non-vessel in angiographic images). Accordingly, different classes of patient and/or image characteristics may be identified, for which different confidence levels could be defined.

In one embodiment, where the primary task is to predict a virtual CFR, the one or more input medical images (received at step 102) may include angiographic images acquired at rest and at hyperemia. The one or more secondary tasks in this embodiment may include the TIMI frame count determined separately for rest and for hyperemia.

Figure 2:
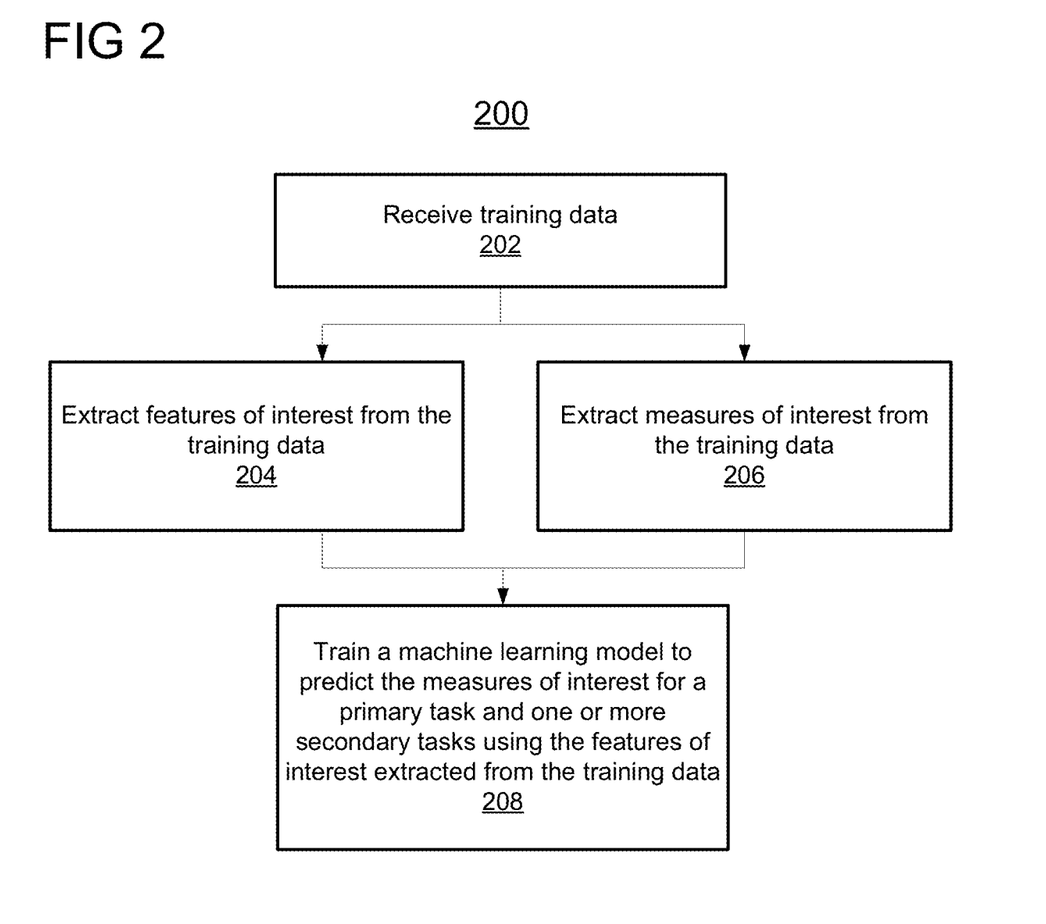
FIG. 2 shows a method for training a machine learning model for predicting measures of interest for a primary task and one or more secondary tasks.

FIG. 2 shows a method 200 for training a machine learning model for predicting measures of interest for a primary task and one or more secondary tasks, in accordance with one or more embodiments. Method 200 is performed during an offline or training stage to train the machine learning model. In one embodiment, the machine learning model trained according to method 200 may be applied during an online or testing stage to perform method 100 of FIG. 1. The steps of method 200 may be performed by any suitable computing device, such as computer 602 of FIG. 6.

At step 202, training data is received. The training data comprises training images labelled (or annotated) with ground truth values. The training images may be of any suitable modality or combination of modalities, such as, e.g., CT, dynaCT, x-ray, MRI, US, etc. The training images may be real images received directly from an image acquisition device (e.g., image acquisition device 614 of FIG. 6), by loading previously acquired medical images from a storage or memory of a computer system, or by receiving medical images that have been transmitted from a remote computer system. The training images may also be synthetically generated training images. In one embodiment, training data also includes patient data.

In one embodiment, the training images comprise pairs (or more) of training images, each selected from a respective sequence of images (e.g., angiograms), along with their mutual angulation information (e.g., angulation of the C-arm of the image acquisition device used to acquire each temporal sequence). In one embodiment, the pairs of training images are selected from their respective sequences of training images by synchronizing the training images in each respective sequence and selecting a synchronized or matching training image from each sequence as the pair of training images, e.g., as described below with respect to FIG. 4.

For each pair of training images, annotations (i.e., ground truth values) are provided to identify measures of interest in the training images. The measures of interest are based on the tasks for which the machine learning model will be trained to perform. For example, the measures of interest may include locations of common image points, stenosis markers, measurement locations, etc. in the training images, as well as FFR values or other hemodynamic metric values (e.g., CFR, iFR, BSR, HSR, IMR, etc.) associated with those locations in the training images. In one embodiment, the annotations are defined as a list of locations (e.g., landmarks) and corresponding FFR values (or other hemodynamic metric values) for each location. An example of a list of annotations is as follows:

Landmark 0: location of a common image point for each image in the pair of training images;
Landmark 1 to N: locations of stenosis markers for each image in the pair of training images;
Landmark N+1 to FFR measurement locations for each image in the pair of
2N+1: training images, ordered consistently with the locations of stenosis markers so that FFR measurement locations can be associated with the corresponding stenosis; and
FFR values 1 to N: FFR values between 0 and 1, ordered consistently with the locations of stenosis markers so that FFR values can be associated with the corresponding stenosis.

The annotated ground truth FFR values may be invasively measured or generated by a virtual FFR predictor (e.g., based on computational modeling or on regression/machine learning). In some embodiments, the training images may be synthetically generated from synthetically generating 3D coronary artery models, e.g., according to known methods.

Figure 3:
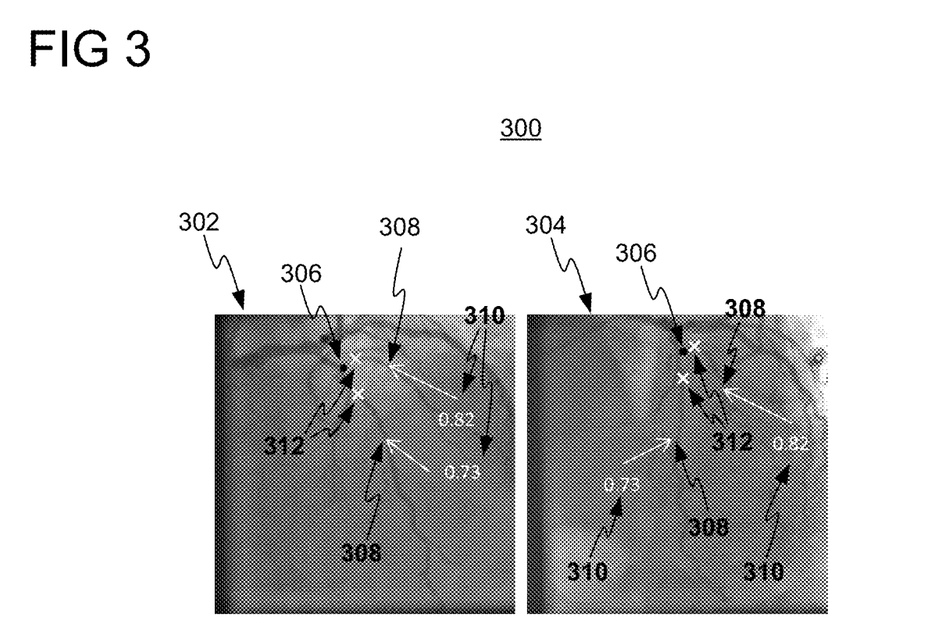
FIG. 3 shows exemplary training data.

FIG. 3 shows exemplary training data 300, in accordance with one embodiment. Training data 300 comprises a pair of training images 302 and 304. Training images 302 may each be from a respective sequence of images. Training images 302 and 304 shows annotations, for illustrative purposes, of common image points 306, stenosis markers 312, and measurement locations 308 with corresponding invasively measured FFR values 310.

At step 204 of FIG. 2, features of interest are extracted from the training data. Generally, the features of interest are implicitly defined by the machine learning model during method 200 for training the machine learning model. For example, image data (e.g., image intensities, pixel values) may be provided directly as input to some dedicated network layers (e.g., convolutional filters in a convolutional neural network) and as part of the training process the parameters of the convolutional filters would be optimized so that the resulting features (i.e., the output of the filters) would be the best predictors for the ground truth labels. Additionally or alternatively, 'handcrafted' features may be used. In one example, such handcrafted features may be determined by splitting the image into patches and (optionally) applying filters to such patches, e.g., to enhance edges. In another example, such handcrafted features may be determined by extracting relevant information from patient data or medical history; for instance defining a vector of categorical variables (e.g., one variable for each pre-existing or related condition such as hypertension, blood cholesterol concentration, etc.) and assigning values to all of the variables depending on the specific patient's history or state. This could be used as an additional 'feature vector' by the network At step 206, measures of interest are extracted from the training data. As noted above, the measures of interest may include, for example, locations of common image points, stenosis markers, measurement locations, FFR values or other hemodynamic metric values (e.g., CFR, iFR, BSR, HSR, IMR, etc.), etc. The measures of interest may be extracted, for example, by parsing the list of annotations. It should be understood that step 206 may be performed at any time prior to step 208 (e.g., before step 204, after step 204, or concurrently with (e.g., in parallel with) step 204).

At step 208, a machine learning model is trained to predict the measures of interest for the primary task and the one or more secondary tasks using the features of interest extracted from the training data. The machine learning models may be trained using any suitable approach, such as, e.g., regression, instance-based methods, regularization methods, decision tree learning, Bayesian, kernel methods, clustering methods, association rule learning, artificial neural networks, dimensionality reduction, ensemble methods, etc. In one example, based on the training data 300 of FIG. 3, the machine learning model may be trained for a primary task to predict virtual FFR values and for a plurality of secondary tasks to predict locations of a common image point, stenosis markers, and measurement locations.

The machine learning model may be based on any suitable machine learning model, such as, e.g., a neural network. In one embodiment, the machine learning model is a deep neural network. For example, the deep neural network may be based on a modified 3D-R2N2 network. The network structure of the trained machine learning model is discussed in further detail below with respect to FIG. 5, in accordance with one embodiment.

In one embodiment, the machine learning model is trained to predict the measures of interest for the primary task and the one or more secondary tasks using multitask learning. Multitask learning is based on the idea that focusing on a single task may prevent the machine learning model from including useful information that would come from learning related tasks. Multitask learning is achieved by parameter sharing in the hidden layers of the machine learning model. The parameter sharing may be, e.g., hard sharing where hidden layers are shared between all tasks while a number of output layers are task specific, or soft sharing where each task has a distinct model with its own parameters but constraints are added to maximize similarity of the parameters across tasks.

In multitask learning, it is important to identify the one or more secondary tasks to maximize performance of the primary task. In one embodiment, the one or more secondary tasks may be identified by, e.g., proposing related tasks to the machine learning model (e.g., proposing the secondary task of predicting anatomical stenosis severity for the primary task of predicting a virtual FFR), identifying the one or more secondary tasks as tasks that predict features that are not easy to learn from the primary task (e.g., identifying the secondary task of predicting whether or not a stenosis is significant for the primary task of predicting a virtual FFR), or identifying the one or more secondary tasks to focus attention to specific portions of the input medical images (e.g., identifying the secondary task of catheter tip detection for the primary task of predicting a virtual FFR, or identifying a secondary task which forces the machine learning model to learn to represent the distance from the coronary ostia).

In the context of predicting a virtual FFR (or other hemodynamic index) as the primary task, multitask learning enables training a unified machine learning model that maps image features of two or more input medical images to a virtual FFR for a detected stenosis. The one or more secondary tasks may include, for example, predicting a location of a stenosis and predicting a location of anatomical landmarks visible in the input medical images. The performance of the one or more secondary tasks may be evaluated (e.g., visually) by a user to thereby evaluate the performance of the machine learning model.

User feedback on the performance of the one or more secondary tasks may be received for online retraining of the machine learning model using interactive machine learning. Interactive machine learning enables a user to provide feedback to the machine learning model, enabling online retraining. Leveraging the multitask learning approach, interactive machine learning may be applied to the one or more secondary tasks (for which user feedback is easier to provide and potentially more robust for inter-user variability) to jointly provide feedback on the performance of the primary task and the one or more secondary tasks.

Figure 4:
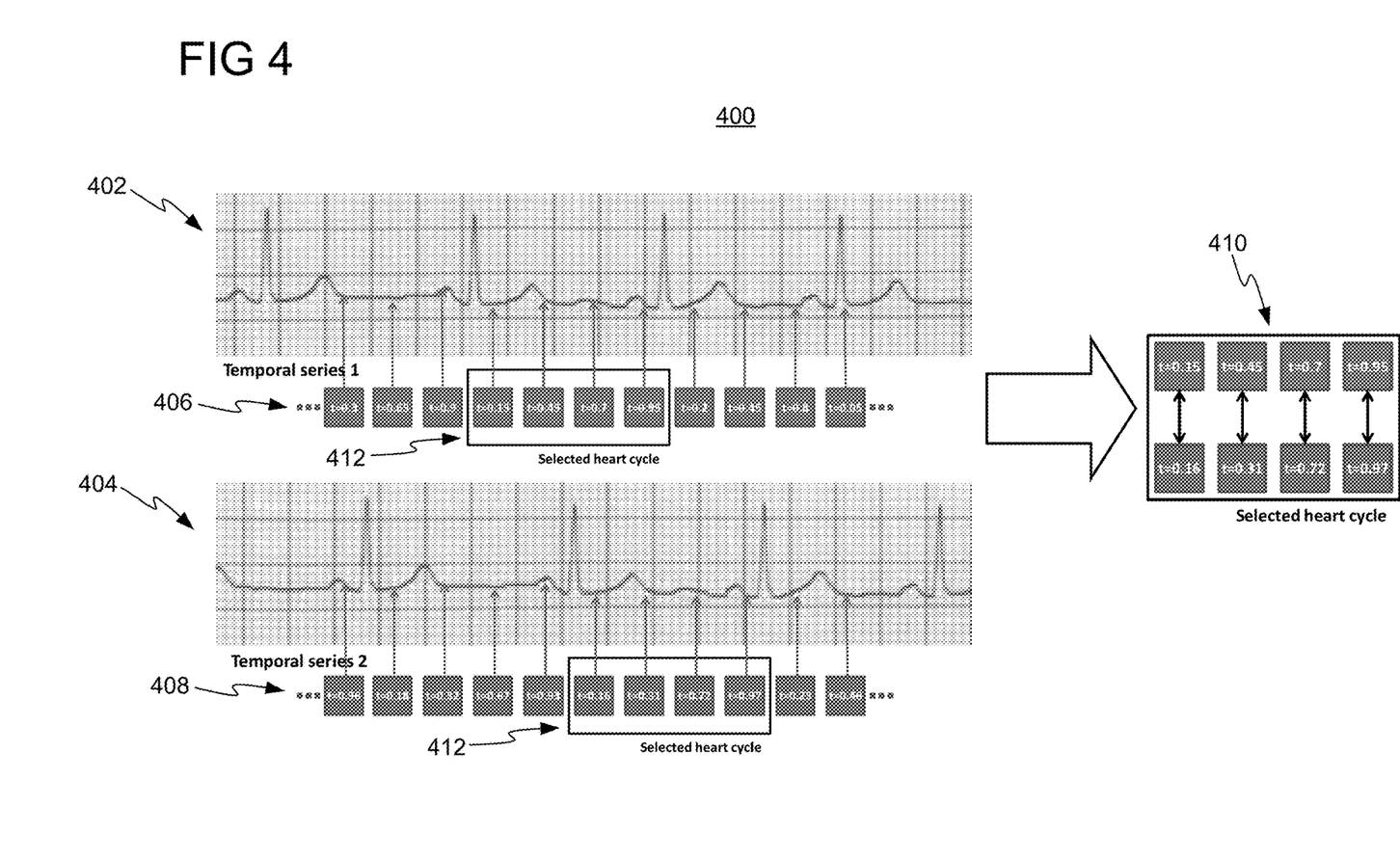
FIG. 4 shows a workflow for synchronizing a first temporal sequence of training images and a second temporal sequence of training images.

FIG. 4 shows a workflow 400 for synchronizing a first sequence of images 406 and a second sequence of images 408, in accordance with one or more embodiments. In one embodiment, workflow 400 may be performed to synchronize images from a sequence of images to determine the one or more input medical images received at step 102 of FIG. 1 or the training data received at step 202 of FIG. 2, in accordance with one embodiment. In another embodiment, the synchronization is one of the one or more secondary tasks and workflow 400 is only performed to prepare the training data for the training stage at step 202 of FIG. 2. While workflow 400 is described as synchronizing a pair of sequences of images, it should be understood that workflow 400 may be applied to synchronize any number of sequences of images.

In workflow 400, electrocardiogram (ECG) signals 402 and 404 of a patient are measured or received during acquisition of the first temporal series (or sequence) of images 406 and the second temporal series of images 408, respectively. An index t is associated with each image of the first temporal series 406 and the second temporal series 408 representing a time relative to a cardiac or heart cycle. In one embodiment, the index is a value between 0 and 1, where 0 represents a beginning of systole and 1 represents an end of diastole, to effectively subdivide the images of temporal series 406 and 408 into a plurality of subsequences each corresponding to one heart cycle.

Images within a subsequence of a selected heart cycle 412 in the first temporal series 406 and the second temporal series 408 are synchronized or matched based on their index to provide synchronized images 410. In one embodiment, images within a subsequence of a selected heart cycle 412 in the first temporal series 406 and a second temporal series 408 are matched where a difference between the indices t associated with the images is minimized. The images are synchronized such that each image in a first temporal series 406 has one and only one corresponding image in the second temporal series 408. The unmatched images may optionally be discarded.

In one embodiment, where ECG signals are not available, the relative time in a heart cycle (e.g., the systole and diastole time) is determined based on the motion of the vessels as depicted in the images, e.g., according to known methods.

Figure 5:
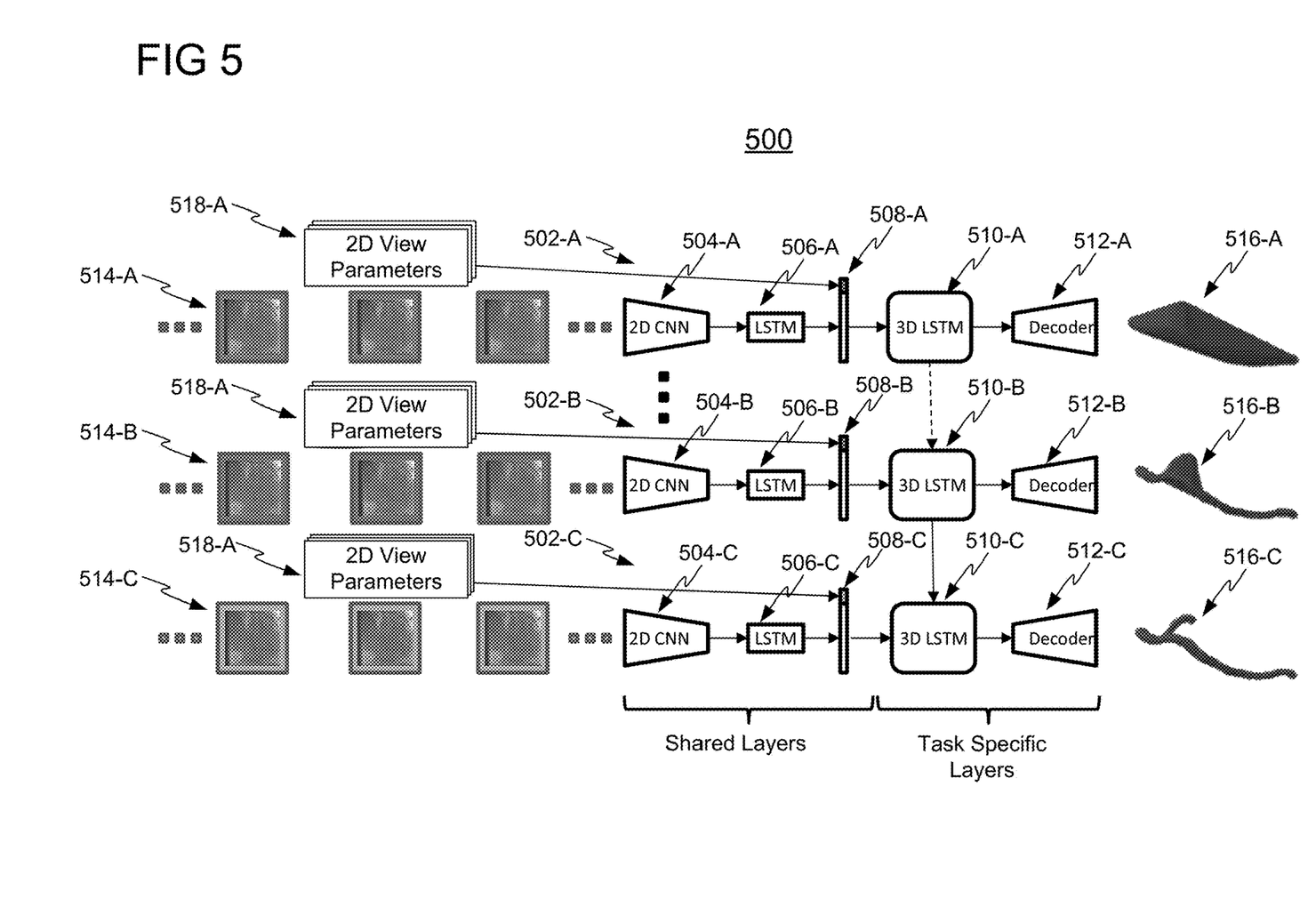
FIG. 5 shows a network architecture of a machine learning model.

FIG. 5 shows a network architecture 500 of a machine learning model, in accordance with one or more embodiments. Network architecture 500 may be the network architecture for the trained machine learning model applied in method 100 of FIG. 1 and trained in method 200 of FIG. 2, in accordance with one embodiment.

Network architecture 500 shows machine learning models 502-A, 502-B, and 502-C (collectively referred to as machine learning model 502). While machine learning models 502-A, 502-B, and 502-C are functionally shown as separate instances in network architecture 500 for ease of understanding to show temporal analysis of input medical images 514-A, 514-B, and 514-C (collectively referred to as input medical images 514), it should be understood that the same machine learning model 502 is applied for each input medical image 514 (i.e., the same machine learning model 502 with the same learned weights are used for each instance of machine learning models 502-A, 502-B, and 502-C to analyze each respective input medical image 514).

Machine learning model 502 receives input medical images 514 depicting vessels and predicts a respective segmentation of the vessels as outputs 516-A, 516-B, and 516-C (collectively referred to as outputs 516). While network architecture 500 shows machine learning model 502 as performing the task of predicting a segmentation of vessels in input medical images 514, it should be understood that machine learning model 502 may additionally or alternatively be trained to perform one or more other tasks (e.g., a primary task and one or more secondary tasks). In one embodiment, machine learning model 502 is a deep neural network. For example, machine learning model 502 may be based on a modified 3D-R2N2 network.

Machine learning model 502 is comprised of 2D convolutional neural networks (CNN) 504-A, 504-B, and 504-C (collectively referred to as 2D CNN 504), long short-term memory (LSTM) recurrent neural networks (RNN) 506-A, 506-B, and 506-C (collectively referred to as LSTM RNN 506), a 3D LSTM network 510-A, 510-B, and 510-C (collectively referred to as 3D LSTM network 510), and decoder 3D deconvolutional neural networks 512-A, 512-B, and 512-C (collectively referred to as decoder 512).

Each input medical image 514-A, 514-B, and 514-C comprises a sequence of images. For example, a respective input medical image 514 may comprise a plurality or all frames of coronary angiographies. Input medical images 514 are fed into machine learning model 502, where they are encoded by 2D CNN 504. The encoded features (from 2D CNN 504) from a plurality of images of the same sequence 514 are aggregated by LSTM RNN 506. The aggregated encoded features from LSTM RNN 506 and 2D view parameters 518-A, 518-B, and 518-C (collectively referred to as 2D view parameters 518) are combined as encoded features 508-A, 508-B, and 508-C (collectively referred to as encoded feature 508), which are input into 3D LSTM network 510. 2D view parameters 518 are features describing the input medical images 514, such as, e.g., C-arm angulation, distance source to detector, image resolution, etc.

3D LSTM network 510 aggregates encoded features 508 from different sequences (e.g., sequences 514-A, 514-B, 514-C) (if any). For example, as shown in network architecture 500, 3D LSTM network 510-B aggregates encoded features 508-B with encoded features 508-A from analysis of input medical images 514-A. In another example, 3D LSTM network 510-C aggregates encoded features 508-C with encoded features 508-A and 508-B from analyses of input medical images 514-A and 514-B. The aggregated encoded features from 3D LSTM network 510 are decoded by decoder 512 to generate outputs 516.

Advantageously, by inputting a sequence of images as input medical images 514, instead of a single image, into machine learning model 502, machine learning model 502 is able to leverage temporal information from the sequence of images. For example, coronary vessels change appearance during the heart cycle due to heart contraction. The sequences of images of input medical images 514 enables machine learning model 502 to learn how the effect of systolic contraction (and its variations across subjects), as seen on the input medical images 514, relates to the 3D geometry of the coronary arteries. In another example, lumen size variation during the heart cycle can also provide an indication of how healthy the arterial wall is. In case of severe atherosclerosis, arterial compliance is almost lost. Machine learning model 502 may learn from this information to further discriminate cases with diffuse or focal disease.

Further, by augmenting encoded features from LSTM RNN 506 with 2D view parameters 518, machine learning model 502 learns how to better discriminate the position of reconstructed vessels in 3D space.

In a multitask learning framework, the different tasks are assumed to be learned by, e.g., hard sharing the layers of the neural network, while additional output layers are task specific. As shown in network architecture 500, machine learning model 502 comprises 2D CNN 504 and LSTM RNN 506 forming an encoding portion of machine learning model 502 having shared layers, and 3D LSTM network 510 and decoder 512 form a decoding portion having task specific layers. Accordingly, machine learning model 502 may be additionally or alternatively trained to perform other tasks by separately training the task specific decoding portion (i.e., 3D LSTM network 510 and decoder 512) for, e.g., predicting a virtual FFR, predicting a location of common image points, predicting measurement locations, predicting a location of a stenosis, etc.

The predicted location in the corresponding 2D input medical images 514 may be determined by projecting the predicted 3D locations to the 2D image planes. For predicting the virtual FFR, additional layers could be trained to map the features of the 3D probability map to FFR values in the entire volume. In one embodiment, the additional layers may be trained based on the methods described in U.S. Pat. No. 9,349,178, issued May 24, 2016, the disclosure of which is incorporated herein by reference in its entirety.

Systems, apparatuses, and methods described herein may be implemented using digital circuitry, or using one or more computers using well-known computer processors, memory units, storage devices, computer software, and other components. Typically, a computer includes a processor for executing instructions and one or more memories for storing instructions and data. A computer may also include, or be coupled to, one or more mass storage devices, such as one or more magnetic disks, internal hard disks and removable disks, magneto-optical disks, optical disks, etc.

Systems, apparatus, and methods described herein may be implemented using computers operating in a client-server relationship. Typically, in such a system, the client computers are located remotely from the server computer and interact via a network. The client-server relationship may be defined and controlled by computer programs running on the respective client and server computers.

Systems, apparatus, and methods described herein may be implemented within a network-based cloud computing system. In such a network-based cloud computing system, a server or another processor that is connected to a network communicates with one or more client computers via a network. A client computer may communicate with the server via a network browser application residing and operating on the client computer, for example. A client computer may store data on the server and access the data via the network. A client computer may transmit requests for data, or requests for online services, to the server via the network. The server may perform requested services and provide data to the client computer(s). The server may also transmit data adapted to cause a client computer to perform a specified function, e.g., to perform a calculation, to display specified data on a screen, etc. For example, the server may transmit a request adapted to cause a client computer to perform one or more of the steps or functions of the methods and workflows described herein, including one or more of the steps or functions of FIGS. 1-2. Certain steps or functions of the methods and workflows described herein, including one or more of the steps or functions of FIGS. 1-2, may be performed by a server or by another processor in a network-based cloud-computing system. Certain steps or functions of the methods and workflows described herein, including one or more of the steps of FIGS. 1-2, may be performed by a client computer in a network-based cloud computing system. The steps or functions of the methods and workflows described herein, including one or more of the steps of FIGS. 1-2, may be performed by a server and/or by a client computer in a network-based cloud computing system, in any combination.

Systems, apparatus, and methods described herein may be implemented using a computer program product tangibly embodied in an information carrier, e.g., in a non-transitory machine-readable storage device, for execution by a programmable processor; and the method and workflow steps described herein, including one or more of the steps or functions of FIGS. 1-2, may be implemented using one or more computer programs that are executable by such a processor. A computer program is a set of computer program instructions that can be used, directly or indirectly, in a computer to perform a certain activity or bring about a certain result. A computer program can be written in any form of programming language, including compiled or interpreted languages, and it can be deployed in any form, including as a stand-alone program or as a module, component, subroutine, or other unit suitable for use in a computing environment.

Figure 6:
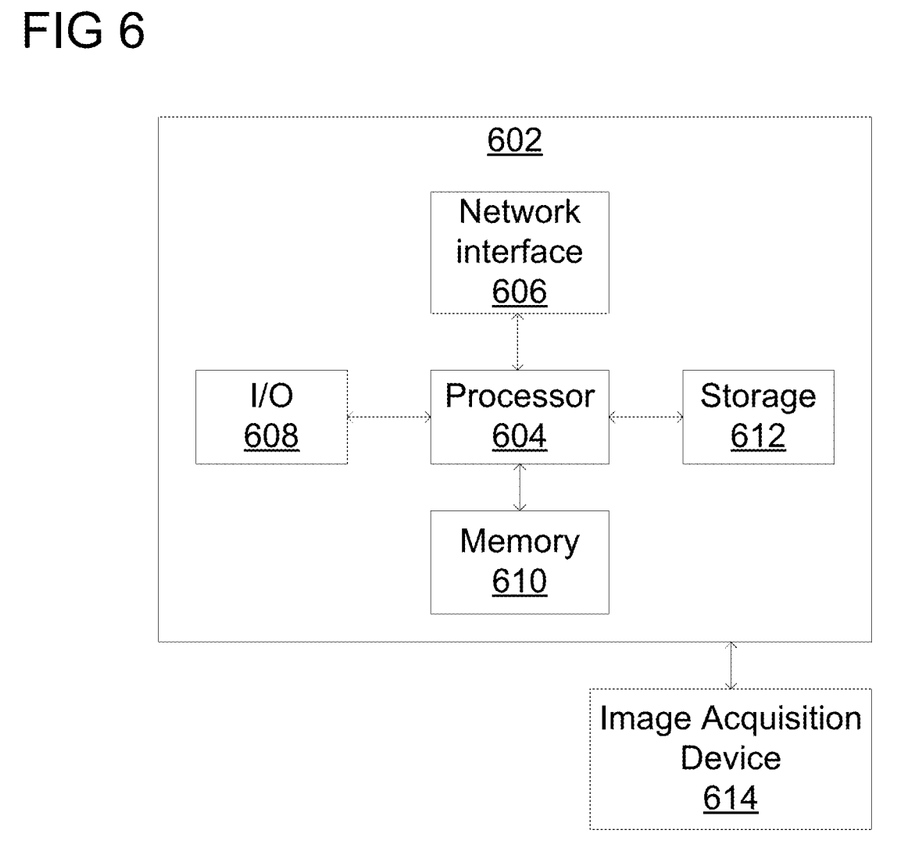
FIG. 6 shows a high-level block diagram of a computer.

A high-level block diagram of an example computer 602 that may be used to implement systems, apparatus, and methods described herein is depicted in FIG. 6. Computer 602 includes a processor 604 operatively coupled to a data storage device 612 and a memory 610. Processor 604 controls the overall operation of computer 602 by executing computer program instructions that define such operations. The computer program instructions may be stored in data storage device 612, or other computer readable medium, and loaded into memory 610 when execution of the computer program instructions is desired. Thus, the method and workflow steps or functions of FIGS. 1-2 can be defined by the computer program instructions stored in memory 610 and/or data storage device 612 and controlled by processor 604 executing the computer program instructions. For example, the computer program instructions can be implemented as computer executable code programmed by one skilled in the art to perform the method and workflow steps or functions of FIGS. 1-2. Accordingly, by executing the computer program instructions, the processor 604 executes the method and workflow steps or functions of FIGS. 1-2. Computer 602 may also include one or more network interfaces 606 for communicating with other devices via a network. Computer 602 may also include one or more input/output devices 608 that enable user interaction with computer 602 (e.g., display, keyboard, mouse, speakers, buttons, etc.).

Processor 604 may include both general and special purpose microprocessors, and may be the sole processor or one of multiple processors of computer 602. Processor 604 may include one or more central processing units (CPUs), for example. Processor 604, data storage device 612, and/or memory 610 may include, be supplemented by, or incorporated in, one or more application-specific integrated circuits (ASICs) and/or one or more field programmable gate arrays (FPGAs).

Data storage device 612 and memory 610 each include a tangible non-transitory computer readable storage medium. Data storage device 612, and memory 610, may each include high-speed random access memory, such as dynamic random access memory (DRAM), static random access memory (SRAM), double data rate synchronous dynamic random access memory (DDR RAM), or other random access solid state memory devices, and may include non-volatile memory, such as one or more magnetic disk storage devices such as internal hard disks and removable disks, magneto-optical disk storage devices, optical disk storage devices, flash memory devices, semiconductor memory devices, such as erasable programmable read-only memory (EPROM), electrically erasable programmable read-only memory (EEPROM), compact disc read-only memory (CD-ROM), digital versatile disc read-only memory (DVD-ROM) disks, or other non-volatile solid state storage devices.

Input/output devices 608 may include peripherals, such as a printer, scanner, display screen, etc. For example, input/output devices 608 may include a display device such as a cathode ray tube (CRT) or liquid crystal display (LCD) monitor for displaying information to the user, a keyboard, and a pointing device such as a mouse or a trackball by which the user can provide input to computer 602.

An image acquisition device 614 can be connected to the computer 602 to input image data (e.g., medical images) to the computer 602. It is possible to implement the image acquisition device 614 and the computer 602 as one device. It is also possible that the image acquisition device 614 and the computer 602 are separate devices communicating (e.g., wirelessly) through a network. In a possible embodiment, the computer 602 can be located remotely with respect to the image acquisition device 614.

Any or all of the systems and apparatus discussed herein, including elements of workstation 102 of FIG. 1, may be implemented using one or more computers such as computer 602.

One skilled in the art will recognize that an implementation of an actual computer or computer system may have other structures and may contain other components as well, and that FIG. 6 is a high level representation of some of the components of such a computer for illustrative purposes.

The foregoing Detailed Description is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the principles of the present invention and that various modifications may be implemented by those skilled in the art without departing from the scope and spirit of the invention. Those skilled in the art could implement various other feature combinations without departing from the scope and spirit of the invention.

The invention claimed is:

1. A method for retraining a trained machine learning model, comprising:
    receiving one or more input medical images;
    predicting measures of interest for a primary task and a secondary task from the one or more input medical images using a trained machine learning model;

outputting the predicted measures of interest for the primary task and the secondary task;
receiving user feedback on the predicted measure of interest for the secondary task; and
retraining the trained machine learning model for predicting the measures of interest for the primary task and the secondary task based on the user feedback on the output for the secondary task.

2. The method of claim 1, wherein the measure of interest for the primary task cannot be directly validated by a user from the one or more input medical images and the measure of interest for the secondary task can be directly validated by the user from the one or more input medical images.

3. The method of claim 1, wherein the user feedback comprises an acceptance or a rejection of the predicted measure of interest for the secondary task.

4. The method of claim 1, wherein the user feedback comprises a modification to the predicted measure of interest for the secondary task.

5. The method of claim 1, further comprising:
predicting additional measures of interest for the primary task and the secondary task from the one or more input medical images using the retrained machine learning model; and
determining a measure of confidence in the predicted additional measures of interest for the primary task and the secondary task based on a difference between the measures of interest predicted using the trained machine learning model and the additional measures of interest predicted using the retrained machine learning model.

6. The method of claim 1, wherein predicting measures of interest for a primary task and a secondary task from the one or more input medical images using a trained machine learning model comprises predicting the measures of interest for the primary task and the secondary task from a single input medical image from a first sequence of images and a single input medical image from a second sequence of images using the trained machine learning model, and the method further comprises:
predicting additional measures of interest for the primary task and the secondary task from two input medical images from the first sequence of images and two input medical image from the second sequence of images using the trained machine learning model; and
determining a measure of confidence in the predicted measures of interest and/or the predicted additional measures of interest for the primary task and the secondary task based on a difference between 1) the measures of interest predicted from the single input medical image from the first sequence of images and the single input medical image from the second sequence of images using the trained machine learning model, and 2) the additional measures of interest predicted from the two input medical image from the first sequence of images and the two input medical image from the second sequence of images using the trained machine learning model.

7. The method of claim 1, wherein the measure of interest for the primary task comprises a hemodynamic index.

8. The method of claim 7, wherein the hemodynamic index is a virtual fractional flow reserve.

9. The method of claim 1, wherein the measure of interest for the secondary task comprises at least one of: a location of a measurement point, a location of a common image point, a location of a stenosis, and a segmentation of a vessel.

10. The method of claim 1, further comprising selecting the one or more input medical images by:
receiving respective electrocardiogram signals acquired during acquisition of a first sequence of images and a second sequence of images;
associating an index with each image in the first sequence of images and the second sequence of images based on their respective electrocardiogram signals;
matching images of the first sequence of images with images of the second sequence of images based on their associated index; and
selecting an image of the first sequence and an image of the second sequence that match as the one or more input medical images.

11. An apparatus for retraining a trained machine learning model, comprising:
means for receiving one or more input medical images;
means for predicting measures of interest for a primary task and a secondary task from the one or more input medical images using a trained machine learning model;
means for outputting the predicted measures of interest for the primary task and the secondary task;
means for receiving user feedback on the predicted measure of interest for the secondary task; and
means for retraining the trained machine learning model for predicting the measures of interest for the primary task and the secondary task based on the user feedback on the output for the secondary task.

12. The apparatus of claim 11, wherein the measure of interest for the primary task cannot be directly validated by a user from the one or more input medical images and the measure of interest for the secondary task can be directly validated by the user from the one or more input medical images.

13. The apparatus of claim 11, wherein the user feedback comprises an acceptance or a rejection of the predicted measure of interest for the secondary task.

14. The apparatus of claim 11, wherein the user feedback comprises a modification to the predicted measure of interest for the secondary task.

15. A non-transitory computer readable medium storing computer program instructions for retraining a trained machine learning model, the computer program instructions when executed by a processor cause the processor to perform operations comprising:
receiving one or more input medical images;
predicting measures of interest for a primary task and a secondary task from the one or more input medical images using a trained machine learning model;
outputting the predicted measures of interest for the primary task and the secondary task;
receiving user feedback on the predicted measure of interest for the secondary task; and
retraining the trained machine learning model for predicting the measures of interest for the primary task and the secondary task based on the user feedback on the output for the secondary task.

16. The non-transitory computer readable medium of claim 15, the operations further comprising:
predicting additional measures of interest for the primary task and the secondary task from the one or more input medical images using the retrained machine learning model; and
determining a measure of confidence in the predicted additional measures of interest for the primary task and the secondary task based on a difference between the measures of interest predicted using the trained machine learning model and the additional measures of interest predicted using the retrained machine learning model.

17. The non-transitory computer readable medium of claim 15, wherein predicting measures of interest for a primary task and a secondary task from the one or more input medical images using a trained machine learning model comprises predicting the measures of interest for the primary task and the secondary task from a single input medical image from a first sequence of images and a single input medical image from a second sequence of images using the trained machine learning model, and the operations further comprises:

predicting additional measures of interest for the primary task and the secondary task from two input medical images from the first sequence of images and two input medical image from the second sequence of images using the trained machine learning model; and determining a measure of confidence in the predicted measures of interest and/or the predicted additional measures of interest for the primary task and the secondary task based on a difference between 1) the measures of interest predicted from the single input medical image from the first sequence of images and the single input medical image from the second sequence of images using the trained machine learning model, and 2) the additional measures of interest predicted from the two input medical image from the first sequence of images and the two input medical image from the second sequence of images using the trained machine learning model.

18. The non-transitory computer readable medium of claim 15, wherein the measure of interest for the primary task comprises a hemodynamic index.

19. The non-transitory computer readable medium of claim 15, wherein the measure of interest for the secondary task comprises at least one of: a location of a measurement point, a location of a common image point, a location of a stenosis, and a segmentation of a vessel.

20. The non-transitory computer readable medium of claim 15, the operations further comprising selecting the one or more input medical images by:

receiving respective electrocardiogram signals acquired during acquisition of a first sequence of images and a second sequence of images;

associating an index with each image in the first sequence of images and the second sequence of images based on their respective electrocardiogram signals;

matching images of the first sequence of images with images of the second sequence of images based on their associated index; and selecting an image of the first sequence and an image of the second sequence that match as the one or more input medical images.

* * * * *